US009416357B2

(12) United States Patent
Stead et al.

(10) Patent No.: US 9,416,357 B2
(45) Date of Patent: Aug. 16, 2016

(54) METHOD FOR ISOLATING TOTAL RNA FROM CELLS

(71) Applicant: UNIVERSITY OF GEORGIA RESEARCH FOUNDATION, INC., Athens, GA (US)

(72) Inventors: Mark B. Stead, Moorpark, CA (US); Sidney R. Kushner, Athens, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 104 days.

(21) Appl. No.: 14/358,596

(22) PCT Filed: Nov. 16, 2012

(86) PCT No.: PCT/US2012/065520
§ 371 (c)(1),
(2) Date: May 15, 2014

(87) PCT Pub. No.: WO2013/074927
PCT Pub. Date: May 23, 2013

(65) Prior Publication Data
US 2015/0218550 A1    Aug. 6, 2015

Related U.S. Application Data

(60) Provisional application No. 61/560,561, filed on Nov. 16, 2011.

(51) Int. Cl.
C07H 21/02 (2006.01)
C12N 15/10 (2006.01)
B01D 15/08 (2006.01)

(52) U.S. Cl.
CPC ............ *C12N 15/1003* (2013.01); *B01D 15/08* (2013.01); *C07H 21/02* (2013.01)

(58) Field of Classification Search
None
See application file for complete search history.

(56) References Cited

U.S. PATENT DOCUMENTS

| | | | |
|---|---|---|---|
| 5,300,635 A | 4/1994 | MacFarlane | |
| 5,728,822 A | 3/1998 | MacFarlane | |
| 5,985,572 A | 11/1999 | MacFarlane | |
| 2008/0057560 A1 | 3/2008 | Chomczynski | |
| 2010/0209930 A1 | 8/2010 | Fernando | |
| 2010/0291536 A1* | 11/2010 | Viljoen | A61B 10/0051 435/4 |

FOREIGN PATENT DOCUMENTS

EP    2363477 A2    9/2011

OTHER PUBLICATIONS

Mahenthiralingam, Eshwar, "Extraction of RNA from Mycobacteria" MycoBacteria Protocols (1998) from Methods in Molecular Biology, vol. 101, pp. 65-75.*
QIAamp® MinElute® Virus Spin Handbook, published 2010 by QIAGEN pp. 3-29.*
Swinson et al., "FORMAzol® as an RNA storage medium: A cautionary note when performing RT-PCR" J. Biochem Biophys. Methods (2005) vol. 63 pp. 149-153.*
Bovre, K. & Szybalski, W. Multistep DNA-RNA hybridization techniques. In Methods Enzymol. XXI, Nucleic Acids, Part D, L. Grossman and K. Moldave, Eds., 350-389 (1971).
Chirgwin, J.M., Przybyla, A.E., MacDonald, R.J. & Rutter, W.J. Isolation of biologically active ribonucleic acid from sources enriched in ribonuclease. Biochemistry 18, 5294-5299 (1979).
Chomczynski, P. & Sacchi, N. Single-step method of RNA isolation by acid guanidinium thiocyanate-phenol-chloroform extraction. Anal Biochem 162, 156-159 (1987).
Chomczynski, P. et al. The single-step method of RNA isolation by acid guanidinium thiocyanate-phenol-chloroform extraction: twenty-something years on. Nature Protocols, 1:2, 581-585 (2006).
Donovan, W.P. & Kushner, S.R. Polynucleotide phosphorylase and ribonuclease II are required for cell viability and mRNA turnover in *Escherichia coli* K-12. Proc Natl Acad Sci U S A 83, 120-124 (1986).
Glisin, V., Crkvenjakov, R. & Byus, C. Ribonucleic acid isolated by cesium chloride centrifugation. Biochemistry 13, 2633-2637 (1974).
MacFarlane, D.E. & Dahle, C.E. Isolating RNA from clinical samples with Catrimox-14 and lithium chloride. Journal of clinical laboratory analysis 11, 132-139 (1997).
MacFarlane, D.E. & Dahle, C.E. Isolating RNA from whole blood—The dawn of RNA-based diagnostics. Nature 362, 186-188 (1993).
Mohanty, B.K, Giladi, H., Maples, V.F. & Kushner, S.R. Analysis of RNA decay, processing, and polyadenylation in *Escherichia coli* and other prokaryotes. Methods Enzymol 447, 3-29 (2008).
O'Hara, E.B. et al. Polyadenylylation helps regulate mRNA decay in *Escherichia coli*. Proc Natl Acad Sci U S A 92, 1807-1811 (1995).
Sevag, M.G., Lackman, D.B. & Smolens, J. The isolation of the components of streptococcal nucleoproteins in serologically active form. J. Biol. Chem. 124, 425-436 (1938).
Stead, M.B. et al. Analysis of *E. coli* RNase E and RNase III activity in vivo using tiling microarrays. Nucleic Acids Res 39, 3188-3203 (2010).
Stead, M.B. et al. RNAsnap™: a rapid, quantitative and inexpensive method for isolating total RNA from bacteria. Nucleic Acids Research, 40:20, 1-9 (2012).
Vincze, E. & Bowra, S. Northerns revisited: a protocol that eliminates formaldehyde from the gel while enhancing resolution and sensitivity. Anal Biochem 342, 356-357 (2005).
Wilfinger, W.W., Mackey, K. & Chomczynski, P. Effect of pH and ionic strength on the spectrophotometric assessment of nucleic acid purity. Biotechniques 22, 474, 476, 478-481 (1997).
International Written Opinion and Search Report from related application PCT/US2012/065520, received Mar. 29, 2013.

* cited by examiner

*Primary Examiner* — Eric Olson
(74) *Attorney, Agent, or Firm* — Meunier Carlin & Curfman LLC

(57) ABSTRACT

Provided herein are methods for isolating cellular ribonucleic acid (RNA) from cells. The method includes suspending cells in an extraction solution comprising formamide; incubating the cells and formamide mixture; and pelleting cell debris, DNA, and protein to form an RNA-containing supernatant. Also provided herein are kits for isolating RNA and solutions for extracting RNA from a cell.

17 Claims, 3 Drawing Sheets

METHOD FOR ISOLATING TOTAL RNA FROM CELLS

CROSS-REFERENCE TO PRIORITY APPLICATION

This application claims priority to U.S. Provisional Application No. 61/560,561, filed Nov. 16, 2011, which is incorporated herein by reference in its entirety.

STATEMENT REGARDING FEDERALLY FUNDED RESEARCH

This invention was made with government support under Grant Number GM081554 awarded by the National Institutes of Health. The government has certain rights in this invention.

BACKGROUND

Historically, working with RNA derived from bacterial cells has been technically difficult because of its highly labile nature and the procedures used for its isolation. Early RNA extractions relied on guanidium isothiocyanate to lyse cells and denature proteins, while the RNA was isolated using a cesium chloride cushion and ultracentrifugation. Subsequently, the use of hot phenol replaced cesium gradients. However, RNA extractions using hot phenol had significant problems both due to the toxicity of the phenol and because the RNA obtained was not consistently of high quality. Accordingly, in the mid 1980s, a protocol was developed that included guanidium isothiocyanate and phenol, which yielded much more reproducible results compared to earlier methods.

Many companies have developed kits making it easier to isolate RNA. These kits, which are relatively expensive, vary greatly in the chemistry and/or mechanics used to lyse the cells, denature and remove proteins, and to isolate the RNA. For example, certain kits use detergents to aid cell lysis and capture RNA and DNA by precipitation. These current RNA isolation procedures contain multiple steps, leading to reduced sample recovery. Furthermore, current RNA isolation methods fail to provide an accurate representation of intracellular RNA pools, since each method appears to selectively enrich for either large or small RNAs relative to the levels of medium sized species. Thus depending on the isolation method used, certain size classes of RNA will be either enriched or depleted relative to the total RNA population.

SUMMARY

Provided herein are methods for isolating cellular ribonucleic acid (RNA) from cells. The method includes suspending cells in an extraction solution comprising formamide; incubating the cells and formamide mixture; and pelleting cell debris, DNA, and protein to form an RNA-containing supernatant. The incubating step can be performed at a temperature of from 10° C. to 140° C. (e.g., 95° C.). The method can further comprise adding zirconium beads prior to incubating the mixture. Optionally, the zirconium beads and the mixture can be mixed or vortexed. Optionally, the method can further include pelleting the cells prior to suspending the cells in the extraction solution.

Optionally, the cells are prokaryotic cells, such as bacterial cells. For example, the bacterial cells can include Gram negative bacterial cells that belong, for example, to the *Escherichia* genus, the *Alcaligenes* genus, the *Serratia* genus, the *Shigella* genus, the *Pseudomonas* genus, the *Salmonella* genus, the *Ruegeria* genus, or the *Myxococcus* genus. In other examples, the bacterial cells can include Gram positive bacterial cells that belong, for example, to the *Bacillus* genus or the *Staphylococcus* genus. Optionally, the cells include archaeal cells or eukaryotic cells. For example, the eukaryotic cells can include yeast cells (e.g., cells that belong to the *Saccharomyces* genus or the *Kluyveromyces* genus) or mammalian cells.

As described above, the extraction solution comprises formamide. The formamide can be present in the extraction solution in an amount of at least 40% by volume of the extraction solution. The extraction solution can further comprise a reducing agent, an anionic detergent, a chelating agent, or a mixture of these. The reducing agent can include, for example, β-mercaptoethanol or dithiothreitol. Optionally, the β-mercaptoethanol is present in the extraction solution in an amount of less than 5% by volume of the extraction solution (e.g., 1% by volume of the extraction solution). Optionally, the dithiothreitol is present in the extraction solution at a concentration of from 50 µM to 1 M. The anionic detergent can optionally include sodium dodecyl sulfate. For example, the anionic detergent can be present in the extraction solution in an amount of less than 5% by weight/volume of the extraction solution (e.g., less than 0.05% by weight/volume of the extraction solution). The chelating agent can include, for example, EDTA. Optionally, the chelating agent is present in the extraction solution at a concentration of from 0.5 mM to 50 mM (e.g., at a concentration of 18 mM). Optionally, the extraction solution is substantially free from quaternary amine surfactants.

The method can further include a step of purifying the RNA from the supernatant. The RNA can be purified by precipitating the RNA and resuspending the RNA in nuclease free water. The RNA can be precipitated using sodium acetate, ammonium acetate, lithium chloride, glycogen, ethanol, isopropanol, or a combination of these (e.g., from sodium acetate and ethanol or from ethanol alone). Optionally, the RNA is purified using a mixture of acidic phenol and chloroform. Optionally, the RNA is purified using column chromatography. Optionally, the method can further include diluting the RNA in nuclease free water.

Also described herein is a kit for isolating RNA from cells. The kit includes a first solution comprising formamide and a second solution comprising β-mercaptoethanol. The first solution can further include an anionic detergent (e.g., sodium dodecyl sulfate), a chelating agent (e.g., EDTA), or a combination of these. Optionally, the kit further includes zirconium beads, a silica column or a glass filter column, and/or nuclease free water.

Further described herein is a solution for extracting RNA from a cell. The solution includes formamide, a reducing agent, an anionic detergent, and a chelating agent. Optionally, the reducing agent includes β-mercaptoethanol. Optionally, the anionic detergent includes sodium dodecyl sulfate. Optionally, the chelating agent includes EDTA.

The details of one or more embodiments are set forth in the accompanying drawings and the description below. Other features, objects, and advantages will be apparent from the description and drawings, and from the claims.

DETAILED DESCRIPTION

Figure 1:
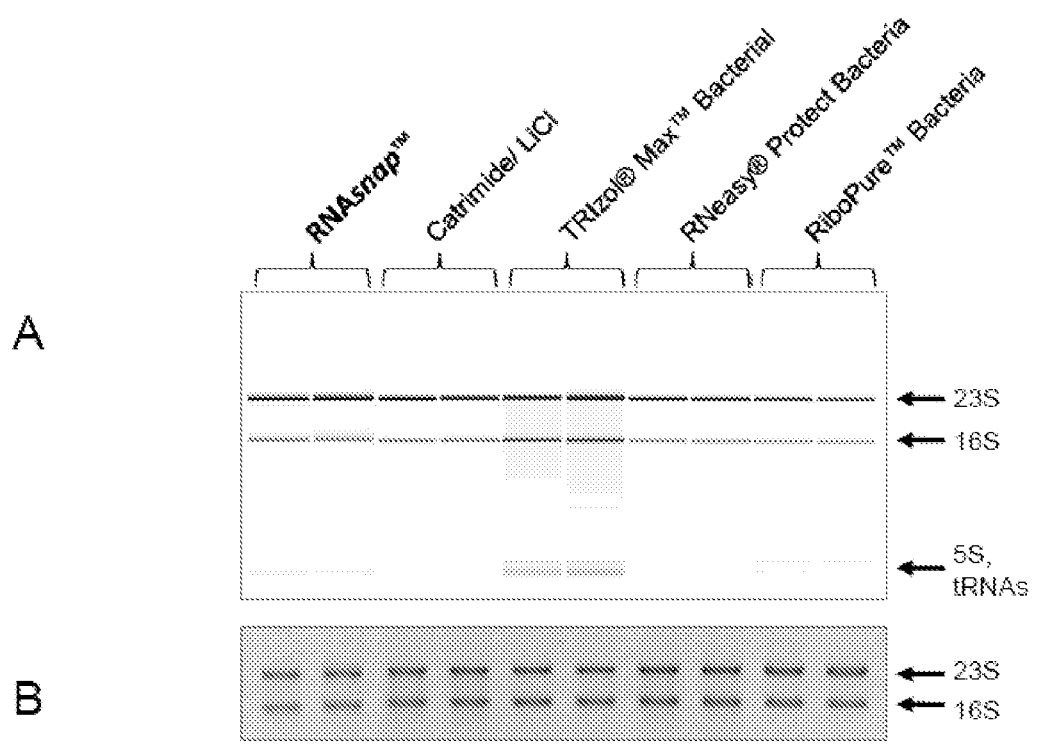
FIG. 1 depicts a RNA quality assessment of RNA samples from each method. Panel A shows a representative composite bioanalyzer digital gel image using two technical replicates of each of the RNA extraction methodologies tested. Panel B shows a representative composite image of technical replicates of 250 ng of total RNA (based on $A_{260}$) from each RNA extraction method electrophoresed on a 1.2% agarose-0.5× TBE gel stained with ethidium bromide.

Described herein are scalable methods for isolating ribonucleic acid (RNA) from biological sources or samples. Suitable biological sources or samples for use in the methods include, for example, cells from a cell culture, isolated biopsy tissue, or environmental samples (e.g., soil or a sample collected from a surface, as by a "wipe test"). The isolation method described here recovers all RNA species from the source. For example, the methods described herein can be used to isolate messenger RNA (mRNA), 16S/18S ribosomal RNA (rRNA), 23S/28S rRNA, 5.8S rRNA, 5S rRNA, transfer RNA (tRNA), small nuclear RNA (snRNA), small nucleolar RNA (snoRNA), micro RNA (miRNA), small interfering RNA (siRNA), trans-acting siRNA (tasiRNA), repeat-associated siRNA (rasiRNA), small temporal RNA (stRNA), tiny non-coding RNA (tncRNA), small scan RNA (scRNA), and small modulatory RNA (smRNA). Optionally, the methods can be used to isolate viral RNA from cells. The results obtained from the method are simple, rapid, and inexpensive to perform and are also highly reproducible. The method includes suspending cells in an extraction solution comprising formamide, incubating the cells and formamide mixture, and pelleting cell debris, DNA, and protein to yield an RNA-containing supernatant. The resulting RNA is of high quality (i.e., lower degradation than with current methods) and quantity (i.e., an improved recovery rate as compared to current methods).

Cells suitable for use in the methods described herein include prokaryotic cells, eukaryotic cells, and archaeal cells. Prokaryotic cells useful herein include, for example, bacterial cells. Optionally, the bacterial cells include Gram negative bacterial cells, such as cells belonging to the *Escherichia* genus, the *Alcaligenes* genus, the *Serratia* genus, the *Shigella* genus, the *Pseudomonas* genus, the *Salmonella* genus, the *Ruegeria* genus, or the *Myxococcus* genus. For example, the bacterial cells can be *Escherichia coli*, *Alcalingenes faecalis* (e.g., ATCC 8750), *Serratia marcescens* (e.g., ATCC 14756), *Shigella flexneri* (e.g., ATCC 9199), *Pseudomonas aeruginosa* (e.g., ATCC 27853), *Salmonella enterica* (e.g., ATCC 29629), *Ruegeria pomeroyi* (e.g., ATCC 700808), or *Myxococcus xanthus* (e.g., DK1622). Optionally, the bacterial cells include Gram positive bacterial cells, such as cells belonging to the *Bacillus* genus (e.g., *Bacillus subtilis* (e.g., ATCC6633)) or the *Staphylococcus* genus (e.g., *Staphylococcus aureus* (e.g., ATCC 6538)). Optionally, the cells include eukaryotic cells. The eukaryotic cells can be, for example, mammalian cells (e.g., cancer cells or normal cells; cells in biological fluids (e.g., plasma, blood, urine, saliva, etc.); or solid tissue samples (e.g., hair, biopsy, cheek swabs, or tissue scrapings)) or yeast cells. Suitable yeast cells include cells belonging to the *Saccharomyces* genus or the *Kluyveromyces* genus.

As discussed above, the methods for isolating cellular RNA include suspending cells in an extraction solution. Optionally, the cells can be pelleted prior to suspending the cells in the extraction solution. The extraction solution comprises formamide. The formamide can be present in the extraction solution in an amount of at least 40% by volume of the extraction solution. For example, the formamide can be present in an amount of at least 45% by volume, at least 50% by volume, at least 55% by volume, at least 60% by volume, at least 65% by volume, at least 70% by volume, at least 75% by volume, at least 80% by volume, at least 85% by volume, at least 90% by volume, or at least 95% by volume.

The extraction solution can further include one or more of a reducing agent, an anionic detergent, and a chelating agent. Reducing agents for use in the extraction solutions include any reducing agent capable of reducing disulfide bonds in cellular proteins. Suitable reducing agents include, for example, β-mercaptoethanol and dithiothreitol. For example, the β-mercaptoethanol can be present in the extraction solution in an amount of less than 5% by volume of the extraction solution. For example, the β-mercaptoethanol can be present in the extraction solution in an amount of less than 4% by volume, less than 3% by volume, less than 2% by volume, less than 1% by volume, or less than 0.5% by volume of the extraction solution. Optionally, dithiothreitol can be present in the extraction solution at a concentration of from 50 μM to 1 M, from 100 μM to 0.5 M, or from 500 μM to 0.1 M.

One or more detergents or surfactants can also be included in the extraction solutions. A detergent refers to a substance having, in combination, a hydrophilic moiety and a hydrophobic moiety. Optionally, the detergent includes an anionic detergent. Suitable anionic detergents include salts of alkyl sulfates, alkyl sulfonates, and bile salts. Optionally, the anionic detergent for use in the extraction solutions described herein includes sodium dodecyl sulfate. Optionally, the anionic detergent is present in the extraction solution in an amount of less than 5% by weight/volume of the extraction solution. For example, the anionic detergent can be present in the extraction solution in an amount of less than 4% by weight/volume, less than 3.5% by weight/volume, less than 3% by weight/volume, less than 2.5% by weight/volume, less than 2% by weight/volume, less than 1.5% by weight/volume, less than 1% by weight/volume, less than 0.5% by weight/volume, less than 0.1% by weight/volume, less than 0.05% by weight/volume, or less than 0.01% by weight/volume of the extraction solution. The extraction solution can be substantially free from quaternary amine surfactants. Substantially free means that the extraction solution can include less than 0.1%, less than 0.01%, less than 0.001%, less than 0.0001%, or 0% of quaternary amine surfactants, or any amount between 0.1% and 0%, based on the weight/volume of the extraction solution.

The extraction solution can further include a chelating agent, such as, for example, ethylenediaminetetraacetic acid (EDTA). The chelating agent is included in a sufficient amount to disrupt secondary and tertiary RNA structures, and to sequester divalent metal ions associated with the activity of ribonucleases. Optionally, the chelating agent is present in the extraction solution at a concentration of from 0.5 mM to 50 mM. For example, the chelating agent can be present in the extraction solution at a concentration of from 1 mM to 40 mM, from 5 mM to 35 mM, from 10 mM to 30 mM, or from 15 mM to 25 mM (e.g., 18 mM).

An exemplary combination of formamide, a reducing agent, an anionic detergent, and a chelating agent to form an extraction solution as described herein includes 95% by volume of formamide, 1% by volume of β-mercaptoethanol, 0.025% by weight/volume of sodium dodecyl sulfate, and 18 mM of EDTA.

The cells can be mixed with the extraction solution. In some examples, the mixture can include $1\times10^8$ cells per 100 μL of extraction solution. Optionally, the number of cells can be increased with the same amount of extraction solution or an incremental increase in the amount of extraction solution. For example, the mixture can include up to $3\times10^8$ cells per 100 μL of extraction solution. Optionally, the mixture can include from $5\times10^8$ cells per 200 μL of extraction solution. Optionally, the mixture can include $1\times10^9$ cells per 500 μL.

Optionally, the method can further include a step of adding zirconium beads to the mixture of the cells and extraction solution. Optionally, the zirconium beads are homogenized with the mixture. The zirconium beads can be added prior to incubating the mixture. The cells and extraction solution can be incubated at a temperature of from 10° C. to 140° C. to lyse the cells. Optionally, the incubating step includes heating the mixture. For example, the incubating step can be performed at a temperature of from 20° C. to 130° C., 30° C. to 120° C., 40° C. to 110° C., or 50° C. to 100° C. (e.g., 95° C.). The incubating step can be performed for a sufficient time to result in cell lysis. Optionally, the cells can be heated from 30 seconds to 1 hour, from 2 minutes to 50 minutes, or from 5 minutes to 30 minutes. The heating can be performed using, for example, a form of dry heat like a sand bath. Optionally, the heating is performed using a paraffin bath, or an oil bath. Optionally, the heating is not performed in a water bath.

The lysed cells can then be pelleted to separate the RNA from the other cellular components, including cell debris, DNA, and protein. Optionally, the lysed cells can be pelleted by centrifuging the mixture at room temperature. In this method, the RNA is present in the supernatant while the cell debris, DNA, and protein are contained in the pellet. The RNA can be isolated by separating the RNA-containing supernatant from the cell pellet. The method can further include diluting the RNA in nuclease free water. Optionally, the RNA can be further purified using, for example, chromatography (e.g., silica gel column chromatography). Optionally, the RNA can be purified by precipitating the RNA obtained from the supernatant and resuspending the RNA in nuclease free water. The RNA can be precipitated using sodium acetate, ammonium acetate, lithium chloride, glycogen, ethanol, isopropanol, or a combination of these. Optionally, the RNA can be precipitated from a combination of sodium acetate and ethanol (e.g., 1 volume of sodium acetate and 3 volumes of ethanol, 2 volumes of sodium acetate and 1 volume of ethanol, or 3 volumes of sodium acetate and 1 volume of ethanol). Optionally, sodium acetate can be excluded from the RNA precipitation. For example, the RNA can be precipitated from ethanol (e.g., 4 volumes of ethanol). Optionally, the RNA can be purified using a mixture of acidic phenol and chloroform followed by an ethanol precipitation.

Also provided herein are kits for isolating RNA from cells. A kit can include a first solution comprising formamide and a second solution comprising β-mercaptoethanol. The first solution can further include an anionic detergent as described herein and/or a chelating agent as described herein. For example, the first solution can include formamide, sodium dodecyl sulfate, and EDTA. Optionally, the kit can further include zirconium beads. Optionally, the kit can further include a silica column or a glass filter column. Optionally, the kit can further include nuclease free water. A kit can additionally include directions for use of the kit (e.g., instructions for preparing the extraction solution or complete instructions for isolating the RNA), a container, and/or a carrier.

Throughout this application, various publications are referenced. The disclosures of these publications in their entireties are hereby incorporated by reference into this application.

The examples below are intended to further illustrate certain aspects of the methods and compositions described herein, and are not intended to limit the scope of the claims.

EXAMPLES

As the interest in RNA metabolism in bacteria has grown, many companies have developed kits making it easier for any laboratory to isolate bacterial RNA. These kits, which are relatively expensive, vary greatly in the chemistry and/or mechanics used to lyse the cells, denature and remove proteins, and to actually isolate the RNA. For example, with respect to cell lysis, the RNeasy® Protect Bacteria Mini Kit (Qiagen; Hilden, Germany) uses an enzymatic digestion step for cell lysis of *Escherichia coli* cultures grown in rich medium. In contrast, the RiboPure™ kit (Ambion; Austin, Tex.) uses mechanical lysis with zirconium beads within a phenol containing lysis buffer, while the TRIzol® Max™ kit (Invitrogen; Carlsbad, Calif.) employs heat in combination with guanidinium isothiocyanate. A quaternary amine-based detergent is used in each of the kits to help lyse the cells and stabilize the RNA by denaturing proteins (Macfarlane et al., *Nature*, 362: 186-188 (1993)).

For the actual isolation of RNA, the RNeasy® Protect Bacteria Mini Kit utilizes a silica column to capture RNA from the lysed sample, wash steps to remove DNA and proteins from the column, followed by elution of the RNA. For both the RiboPure™ Bacteria kit and TRIzol® Max™ Bacteria Kit, the RNA is separated by using a phenol/chloroform extraction step to aid in protein/DNA/RNA separation and subsequent RNA stability. Subsequently, the RiboPure™ Bacteria kit uses a glass filtration column followed by washes and RNA elution, which is similar to other column-based RNA extraction methods. In contrast, the TRIzol® Max™ Bacteria kit employs an isopropanol-based RNA precipitation to recover the RNA following the phenol/chloroform extraction.

The use of detergents to promote cell lysis has been used to capture RNA and DNA by precipitation (MacFarlane et al, *Nature*, 362:186-188 (1993); MacFarlane et al., *Journal of Clinical Laboratory Analysis*, 11: 132-139 (1997); O'Hara et al., *Proc Natl Acad Sci USA*, 92:1807-1811 (1995)). DNA in the pellet is subsequently removed by washing with LiCl, which takes the place of detergent in interacting with RNA, but does not effectively precipitate DNA (Macfarlane et al., *Journal of Clinical Laboratory Analysis*, 11: 132-139 (1997)). The surfactant trimethyl(tetradecyl)ammonium bromide (subsequently called catrimide) has been used for such purposes (Mohanty et al., *Methods Enzymol*, 447: 3-29 (2008)).

Current RNA isolation procedures contain multiple steps, leading to reduced sample recovery. Furthermore, although each manufacturer provides specifications for the yield and RNA quality resulting from their procedure, there has not previously been an actual side-by-side comparison of the various methods in terms of total RNA yield, RNA quality, size distribution of the RNA molecules, time to carry out the procedure, and cost per sample. In fact, upon examination of the different RNA samples obtained using various kits and in-house experience with the catrimide/LiCl method, it was apparent that none of the current RNA isolation methods provide an accurate representation of intracellular RNA pools, since each method appears to selectively enrich for either large or small RNAs relative to the levels of medium sized species. Thus depending on the isolation method used, certain size classes of RNA will be either enriched or depleted relative to the total RNA population.

In contrast, the procedure described herein quantitatively retains all RNA species. The isolation method is remarkably simple, rapid, reproducible, and inexpensive. With Gram-negative bacteria, Gram-positive bacteria, and yeast, the method yields high quality RNA in less than 15 minutes that can be used directly (i.e., without any further purification) for both polyacrylamide and agarose Northern analysis.

Bacterial Strains

*E. coli* strain MG1693 (thyA715 rph-1) (provided by the *E. coli* Genetic Stock Center, Yale University) was grown with shaking at 37° C. in Luria broth supplemented with thymine (50 μg/ml) to exactly 50 Klett units above background (No. 42 green filter or $OD_{600}$ 0.4), which is approximately $10^8$ cfu/ml.

RNA Isolation Methods: Example 1 and Comparative Examples

Example 1

One ml of bacterial culture ($10^8$ cells) was used for each RNA isolation sample. Each RNA extraction method was performed with a minimum of two independent biological replicates and at least four technical replicates to measure reproducibility. For the method described herein, one ml of culture was centrifuged at 16,000×g for 30 seconds and the supernatant was removed by aspiration. The cell pellet was stored in dry ice until ready for extraction. Cell pellets were then re-suspended in 100 μl of RNA extraction solution [18 mM EDTA, 0.025% SDS, 1% β-mercaptoethanol, 95% Formamide (RNA grade)] by vortexing vigorously. The cells were lysed by incubating the sample at 95° C. in a sand bath for seven minutes. The cell debris was pelleted by centrifuging the warm sample at 16,000×g for 5 minutes at room temperature. The RNA was in the supernatant and the gelatinous pellet contained protein, cell debris and the majority of the DNA. The supernatant was carefully transferred to a fresh tube without disturbing the clear gelatinous pellet.

Comparative Examples

The catrimide/LiCl method for RNA extraction used for these experiments was performed similarly to the method described by Mohanty et al., *Methods Enzymol*, 447:3-29 (2008), but was modified for one ml samples. Briefly, one ml of bacterial culture was added to 500 μl of stop buffer, which was previously frozen horizontally in a 1.7 ml microcentrifuge tube. The cells were immediately mixed by vortexing vigorously, and then pelleted by centrifugation at 5,000×g for 5 minutes at 4° C. The supernatant was carefully removed by aspiration, and the pellet was suspended in 200 μl of lysis buffer by vortexing. The sample was then placed into a dry-ice ethanol slurry for 90 seconds, and followed by 90 seconds of incubation in a 37° C. water bath. This freeze-thaw cycle was repeated four times in total. After the fourth 37° C. incubation, the sample was transferred into the dry ice-ethanol slurry in order to refreeze the solution, and 35 μl of 20 mM acetic acid was then added to the frozen solution. The sample was then placed back into the 37° C. water bath, followed by addition of 200 μl of 10% Catrimide [(trimethyl(tetradecyl) ammonium bromide)] when the sample was almost completely thawed. The sample was briefly vortexed and centrifuged at 16,000×g for 10 minutes at 4° C. The supernatant was carefully removed by aspiration, and the pellet was suspended in 500 μl of 2M LiCl in 35% ethanol by vortexing very vigorously. The sample was then incubated at room temperature for 5 minutes, followed by centrifugation at 16,000×g for 10 minutes at 4° C. The supernatant was carefully removed by aspiration and the pellet was resuspended in 500 μl of 2 M LiCl in water followed by a repeat centrifugation.

The pellet was briefly vortexed in 75% ethanol and centrifuged at 8,000×g for 5 minutes at 4° C. The ethanol was removed by aspiration, and the tube was briefly centrifuged for a second time in order to collect and remove the remaining ethanol with a pipette. The pellet was allowed to air dry at room temperature for 10 minutes and subsequently hydrated by the addition of 100 μl of RNase-free water and incubated at room temperature for 10 minutes. The tube was vigorously vortexed, centrifuged at maximum force (21,000×g) at room temperature for 1 minute to pellet cell debris, and the RNA containing supernatant was transferred to a new tube.

All other RNA extraction methods were done according to the manufacturer's recommendations and protocols specific for the number of *E. coli* cells and conditions in which they were grown. Any step described as optional, but that might improve the quality or yield of RNA was followed. No optional DNase I treatment was performed on any RNA sample used in this study. Every effort was made to ensure that the extracted RNA using each method met the manufacturer's guidelines in terms of overall RNA yield, $A_{260}/A_{280}$ ratio, and RNA quality.

Determination of RNA Quantity and Quality: Example 1 and Comparative Examples

In most RNA isolation methods, the amount of RNA present is initially determined based on absorbance at 260 nm ($A_{260}$) or through the use of fluorescent dyes. Although these approaches provide an accurate estimate of the RNA present in a particular sample, the relative amounts of each RNA species can vary widely depending on the particular isolation method employed. These variations are due to properties of many RNA isolation procedures, which are biased towards either large (i.e., rRNA or large mRNAs) or small (tRNAs and sRNAs) RNAs associated with all of the current RNA isolation procedures. Thus, it is not possible to accurately assess the in vivo distribution of the various classes of RNA molecules in a particular sample. In order to help address the problem of representative and quantitative recovery, a one-step RNA extraction procedure was developed that took place in a single tube in which total RNA was quantitatively recovered in the supernatant and the bulk of the DNA and proteins were left in the pellet. Losses associated with multiple handling steps were eliminated.

RNA quantity and $A_{260}/A_{280}$ ratios were determined using a Nanodrop 2000c (Thermo Scientific). The amount of RNA in the Example 1 supernatants was determined by $A_{260}$, using the RNA extraction solution as a blank. The RNA extraction solution was made fresh and was also used as the blank, since the $A_{260}$ of the extraction solution itself changed over time after the addition of β-mercaptoethanol. RNA quality was assessed by running 250 ng of each RNA sample, as determined by $A_{260}$, on a 1.2% agarose-0.5×TBE gel with Ethidium Bromide, run at 5 v/cm for 1 hour. RNA samples were denatured prior to loading by suspension in Gel Loading Buffer II (Ambion) and heating for 5 minutes at 95° C. Approximately 100 ng of each RNA sample were subsequently analyzed on a Bioanalyzer RNA chip (Agilent Technologies) using the manufacturer's recommendations.

For Example 1, a one ml sample of an early exponential culture of *E. coli* ($10^8$ cells) yielded ~60±3 ug of total RNA with the entire procedure taking less than 15 minutes (see Table 3). The quality of the RNA derived from the Example 1 was as good or better than RNA obtained by the comparative example methods tested in this study and was suitable, without any further treatment, for Northern analysis using either polyacrylamide or agarose gels (see FIG. 2). The genomic DNA contamination in the Example 1 sample was comparable to that obtained with the other isolation methods.

Quantitative Determination of RNA Recovery Using the Example 1 Method

Even though the procedure described in Example 1 was rapid and yielded more total RNA per cell than any of the comparative methods tested (see Table 3), it was important to determine how much RNA remained in the gelatinous pellet after extraction was carried out. Accordingly, the isolation was scaled up to 10 ml of culture ($10^9$ cells), again carried out in a single tube. Specifically, in order to estimate the amount of RNA remaining in the pellet, an extraction according to Example 1 was performed using 10 ml of *E. coli* cells ($10^8$ cells/ml) using 500 μl of RNA extraction solution. After the supernatant containing the RNA was recovered and placed into a separate tube, an additional 500 μl of room temperature RNA extraction solution was gently added to the gelatinous pellet in order to wash the pellet of the RNA containing supernatant, which could not be initially removed without disturbing the pellet. The tube was then spun at 16,000×g for an additional five minutes and the supernatant was again removed without disturbing the pellet. The pellet was then suspended in 100 μl of RNase-free water. Subsequently, another 100 μl of acidic phenol/chloroform (Ambion, 5:1 solution, pH 4.5) was added and the tube was vortexed vigorously for 30 seconds. The tube was then centrifuged at 16,000×g for five minutes and the aqueous phase was transferred to a fresh tube and sodium acetate/ethanol precipitated. The precipitated RNA was hydrated in 20 μl of RNase-free water. After the RNA was fully dissolved, the total amount of RNA was determined based on $A_{260}$ and was compared with the amount of RNA in the first 500 μl volume of RNA extraction solution recovered from the pellet.

Two hundred and fifty ng of RNA from both the re-extracted pellet and the original supernatant were run on an agarose gel to confirm the presence, quality, and quantity of the RNA. In each of two replicates, approximately 2.5 μg of high quality RNA was recovered from the re-extracted pellet, while >700 μg of RNA was found in the supernatant, indicating that the efficiency of RNA recovery from *E. coli* using the Example 1 method was greater than 99%. Additionally, the profile of the various abundant RNA species (tRNAs, 5S rRNA, sRNAs,16S rRNA and 23S rRNA) was identical between the two RNA samples upon visual inspection of the agarose gel.

In an attempt to determine the size distribution of the transcripts present in the RNA isolated using the Example 1 method, the RNA obtained was compared with RNA isolated by the comparative methods, including the catrimide/LiCl method and three of the most widely used commercially available RNA isolation kits (i.e., TRIzol® Max™ Bacteria (Invitrogen), RNeasy® Protect Bacteria (Qiagen) and RiboPure™ Bacteria (Ambion)). Each extraction method was tested using at least two independent biological replicates and two or more technical replicates per biological replicate. The quality of each RNA sample was assessed using three main criteria: purity as determined by a spectrophotometer ($A_{260/280}$ ratio), the 23S rRNA/16S rRNA ratio as determined by Bioanalyzer analysis (Agilent Technologies), and an RNA integrity score derived from Bioanalyzer analysis.

As shown in FIG. 1, the quality of the RNA derived from using the Example 1 method was as good as or better than RNA obtained by the other methods tested based on both Bioanalyzer analysis (Agilent Technologies) (FIG. 1A; Table 1) and agarose gel electrophoresis (FIG. 1B). The ratio of *E. coli* 23S to 16S rRNA in the samples isolated by the Example 1 method was 1.8, which came closer to the theoretical ratio of 1.88 (2904 nt/1541 nt) than any other method tested (Table 1). $A_{260/280}$ ratio of ~2.0 for all the RNA preparations (Table 1) indicated that all of the samples were relatively pure with the exception of the Example 1 sample obtained in one step. An $A_{260/280}$ ratio of 1.8-2 is indicative of highly purified RNA when resuspended in a buffered solution like TE (pH 8.0). However, this ratio is highly dependent on pH and the pH of the Example 1 RNA sample was not 8.0. Accordingly, resuspension of the RNA in RNase-free water after a sodium acetate/ethanol precipitation significantly improved the ratio (Table 1; see Example 1 Precipitated). Additionally, diluting the Example 1 RNA sample with RNase free water also improved the $A_{260/280}$ ratio such that it was comparable to the other methods shown in Table 1.

There were significant differences in terms of the amounts of the rRNAs and tRNAs present as well as RNA integrity scores (Table 1). The Example 1 method, the catrimide/LiCl method, the RiNeasy® method, and the Ribopure™ method yielded comparable amounts of 16S and 23 S rRNAs, which were significantly higher than what was observed with the TRIzol® Max™ Bacteria method (Table 1). In contrast, the TRIzol® Max™ Bacteria method yielded the highest concentrations of 5S rRNA and tRNAs, followed by the Example 1 method (FIG. 1B).

TABLE 1

| Catrimide/ LiCl | TRIzol ® Max ™ Bacteria | RNeasy ® Protect Bacteria | RiboPure ™ Bacteria | Example 1 | Example 1 Precipitated |
|---|---|---|---|---|---|
| $A_{260/280}$ | | | | | |
| 2.00 ± 0.01 | 1.97 ± 0.02 | 2.13 ± 0.01 | 2.12 ± 0.02 | 1.73 ± 0.01 | 1.92 ± 0.02 |
| 23S rRNA/16S rRNA | | | | | |
| 1.73 ± 0.15 | 1.21 ± 0.05 | 2.38 ± 0.55 | 2.05 ± 0.16 | 1.80 ± 0.01 | 1.21 ± 0.08 |
| RNA integrity # | | | | | |
| 9.4 ± 0.29 | 7.9 ± 0.17 | 9.0 ± 0.52 | 9.4 ± 0.21 | 9.5 ± 0.00 | 9.5 ± 0.35 |

Northern Analysis

Since there were differences in the distribution of RNAs among of the most abundant RNA size classes obtained from the various RNA isolation methods, the differences for specific RNA molecules ranging in size from 76-5700 nt were quantified using Northern analysis. Two types of Northern blots were performed in this study, a 6% polyacrylamide/8.3 M Urea 1×TBE gel for small RNA species (lpp, cspE, 5S rRNA, ryhB, and pheU/pheV), and a 1.2% Agarose 1×MOPS gel for larger species (rpsJ operon, adhE, and ompF). Northern analysis was performed as described in Stead et al., *Nucleic Acids Res*, 39: 3188-3203 (2010). The RNA present in the supernatants obtained from the Example 1 method was used directly for polyacrylamide gels after dilution to the desired loading volume in a formamide based RNA loading dye. For agarose Northerns, the RNA in the extraction solution was brought up to a total volume of 10 μl with Example 1 RNA extraction solution. Subsequently, 4 μl of loading solution (3.8 μl of any formamide-based RNA loading dye along with 0.2 μl of 37% formaldehyde) were added. The samples were heated at 65° C. for five minutes and placed on ice for one minute followed by brief centrifugation before loading onto a 1.2% Agarose 1×MOPS gel, similar to the method of Vincze et al., *Anal Biochem*, 342: 356-357 (2005). Subsequently, the RNA was transferred to a positively charged nylon membrane by electroblotting.

The Northern membranes were subsequently probed with multiple $^{32}$P-labeled oligonucleotide probes such that the signal for lpp, SS rRNA, and pheU/V were simultaneously visualized on a single membrane (similarly for cspE/ryhB and adhE/ompF). This approach helped determine if loading errors could account for differences in signal between the two replicates, as the percentage difference should be the same for each of those RNA species probed in the same lanes, unless the RNA extraction method used caused non-quantitative recovery of a particular RNA species. It was also technically possible that an error during the transfer of RNA from the gel to the nitrocellulose membrane accounted for a difference between replicates, but this type of error is extraordinarily rare with polyacrylamide Northerns, and occurs infrequently with agarose Northerns. The data were obtained using a GE Storm PhosphorImager and quantified using ImageQuant TL software. The values obtained for the Catrimide RNA were set at 1 and used to normalize the other RNA samples. Each relative abundance value is the average of at least two independent replicates.

Due to the differences in the distribution of RNAs among the most abundant RNA size classes obtained from the various RNA isolation methods (FIG. 1), the relative abundances of specific RNA molecules ranging in size from 76 to >5700 nt were determined using Northern analysis. Since the Example 1 method resulted in over 99% of total cellular RNA, the relative abundance of each of the transcripts derived from other methods (FIG. 2A) was calculated relative to that obtained from the Example 1 method (Table 2). Transcripts greater than 100 nt (ompF, adhE, and the rpsJ operon) were less abundant in the TRIzol® Max™ RNA method compared to any of the other methods (Table 2). In fact, the recovery of the larger transcripts decreased gradually as a function of increased size leading to very low recovery of the ~5700 nt rpsJ operon nRNA (the largest transcript tested). Furthermore, the variability from one isolation to another using the TRIzol® Max™ method was also very high for larger transcripts (FIG. 2; Table 2). In contrast, all the other RNA isolation methods contained the larger species at levels that were 1.6-4.4 fold higher than the RNA obtained by the Example 1 method.

Figure 2:
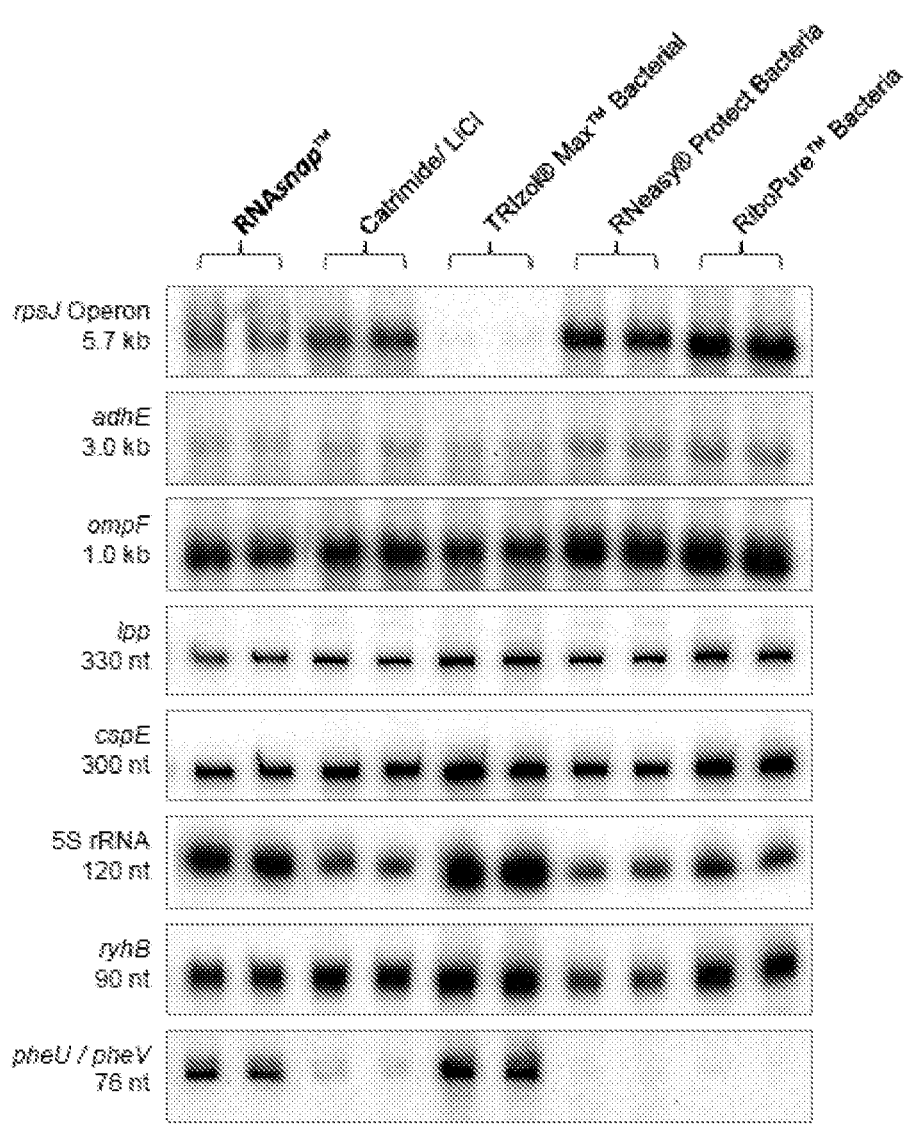
FIG. 2 depicts a Northern analysis of specific RNA species using total RNA pool isolated by each RNA isolation method. Five μg of total RNA (based on $A_{260}$ and two independent technical replicates) was used for Northern analysis on each of the eight specific RNAs listed on the sides of the autoradiograms along with the approximate size of each transcript.

At the lower end of the RNA size spectrum, i.e., transcripts smaller than 300 nt (pheU/pheV, ryhB, 5S rRNA), the RNeasy®Protect Bacteria, Ribopure™, and catrimide/LiCl methods yielded significantly less RNA with up to 20-fold decreases for some species (FIG. 2; Table 2). The exception was the ryhB small regulatory RNA, which was present in comparable amounts in all five RNA samples (Table 2). The TRIzol® Max™ sample consistently had between 1.4-2 fold higher levels of all three small RNAs tested (Table 2). For the two species in the 300 nt range (cspE and lpp), all five methods gave comparable levels (Table 2), within experimental error.

Overall, of the commonly used RNA isolation kits, TRIzol® Max™ was the best for isolating small RNAs, but it selectively lost larger RNA species (Table 2). In the case of the RNeasy® Protect Bacteria, Ribopure™, and catrimide/LiCl RNA samples, small RNAs were either underrepresented (catrimide/LiCl) or almost completely absent (RNeasy®Protect Bacteria and Ribopure™).

TABLE 2

| RNA transcript | RNA ~size (nt) | Example 1 | TRIzol® Max™ Bacteria | RNeasy® Protect Bacteria | RiboPure™ Bacteria | Catrimide/LiCl |
|---|---|---|---|---|---|---|
| pheU/V | 76 | 1 ± 0.0 | 1.64 ± 0.11 | 0.09 ± 0.11 | 0.05 ± 0.05 | 0.15 ± 0.10 |
| ryhB | 90 | 1 ± 0.0 | 1.39 ± 0.56 | 0.8 ± 0.26 | 1.68 ± 0.33 | 1.01 ± 0.55 |
| 5S rRNA | 120 | 1 ± 0.0 | 1.99 ± 0.13 | 0.35 ± 0.01 | 0.77 ± 0.34 | 0.45 ± 0.10 |
| cspE | 300 | 1 ± 0.0 | 1.67 ± 0.0 | 1.04 ± 0.14 | 1.86 ± 0.50 | 0.93 ± 0.22 |
| lpp | 330 | 1 ± 0.0 | 2.03 ± 0.16 | 1.24 ± 0.08 | 1.64 ± 0.02 | 1.09 ± 0.05 |
| ompF | 1000 | 1 ± 0.0 | 0.81 ± 0.47 | 1.51 ± 0.40 | 1.94 ± 0.11 | 1.40 ± 0.46 |
| adhE | 3000 | 1 ± 0.0 | 0.53 ± 0.10 | 1.67 ± 0.11 | 2.62 ± 0.90 | 1.24 ± 0.44 |
| rpsJ operon | 5700 | 1 ± 0.0 | 0.47 ± 0.36 | 2.60 ± 0.33 | 4.37 ± 0.33 | 1.62 ± 0.48 |

Generality of Example 1 RNA Isolation Method

Isolation of RNA from stationary phase cells using current methods has been difficult. In contrast, the Example 1 method worked equally well with late stationary phase cells, unlike what has been observed with the catrimide/LiCl extraction procedure. In addition, the Example 1 procedure was easily and quantitatively scaled to handle 10 ml of culture ($10^9$ cells) for situations where larger amounts of RNA were needed.

Furthermore, the Example 1 RNA was used directly in polyacrylamide/urea and agarose gels without further purification. However, due to the nature of the RNA extraction solution, the RNA species (>1000 nt) reproducibly appeared larger on formaldehyde agarose gels than their actual size (as shown in FIG. 2B). The Example 1 RNA sample was first diluted with two volumes of water followed by addition of 1/10 volume of 3 M sodium acetate, pH 5.2 and the sample was mixed by pipetting. Three volumes of 100% ethanol were then added, the sample was mixed briefly by vortexing, and was incubated for at least 60 minutes at −80° C. The tube was centrifuged at 16,000×g for 30 min at 4° C. The supernatant was carefully removed by aspiration and the pellet was washed with 250 µl of 75% ethanol, centrifuged at 8,000×g for five minutes at 4° C. The supernatant was removed via aspiration and the tube was briefly centrifuged again. Following the removal of any remaining ethanol, the pellet was air dried. The pellet was resuspended in water and centrifuged at 16,000×g for one minute to pellet any remaining water insoluble proteins, and the RNA containing supernatant was transferred to a fresh tube. Once the RNA was precipitated out of the extraction solution and re-suspended in water (see Methods), the electrophoretic mobilities of all RNA species were normal.

The Example 1 method has been used to successfully isolate RNA from a number of other Gram negative bacteria including: *Alcalingenes faecalis* (ATCC 8750); *Serratia marcescens* (ATCC 14756); *Shigella flexneri* (ATCC 9199); *Pseudomonas aeruginosa* (ATCC 27853); *Salmonella enterica* (ATCC 29629); *Ruegeria pomeroyi* (ATCC 700808) and *Myxococcus xanthus* DK1622. Additionally, using a slightly modified version of the Example 1 method in which zirconium bead homogenization was added for lysis efficiency, high quality RNA was obtained from two Gram positive bacteria: *Bacillus subtilis* (ATCC 6633) and *Staphylococcus aureus* (ATCC 6538). The modified method also worked with both *Saccharomyces cerevisiae* and *Kluyveromyces lactis*.

Overview of the Five RNA Isolation Procedures

Figure 3:
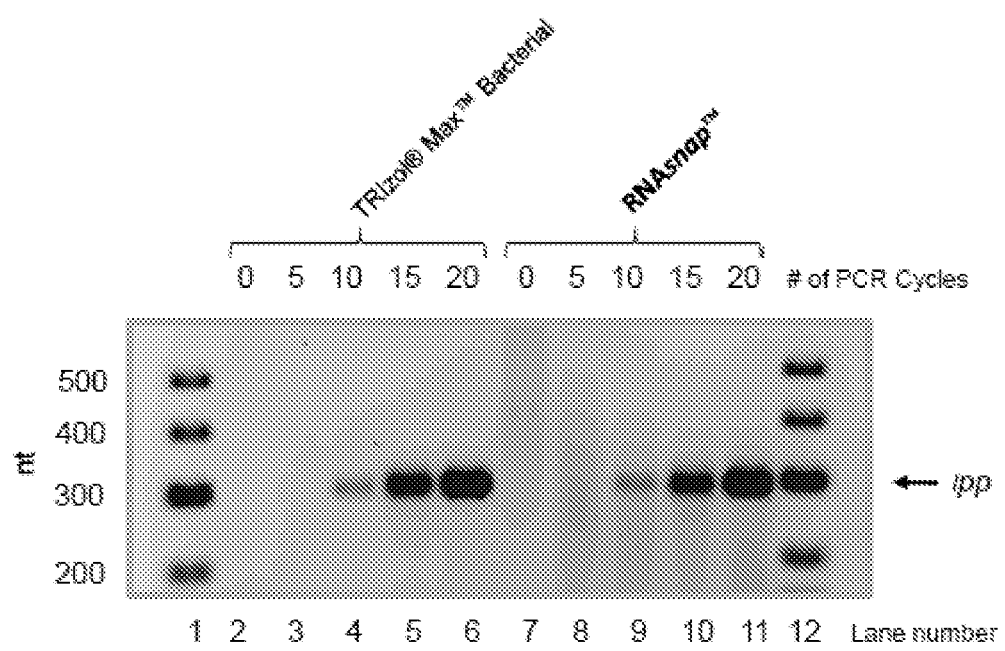
FIG. 3 depicts a comparison of RNA isolated using the Example 1 method and using TRIzol® Max™ in a RT-PCR experiment. RNA isolated from SK4390 (rph-1 ΔrppH) was reverse transcribed with a primer specific for the lpp mRNA (~330 nt) and subsequently PCR amplified for either 5, 10, 15, or 20 cycles. The amplified PCT products were run on a 2% agarose gel (lanes 2-10). Lanes 1 and 12, Gene Ruler™ Low Range DNA Ladder (Fermentas Inc.; Glen Burnie, Md.).

As shown in Table 3, the Example 1 method provided the highest total RNA yield of all five isolation procedures (1.7-4-fold higher). A comparison of the cost per sample, time to complete the RNA isolation and the recommended size range for efficient recovery of specific RNA transcripts, as tested in this study, is shown in Table 3. Cost per sample ranged from over $8.00 for the RNeasy® Protect Bacteria kit to approximately three cents for the Example 1 method. The Example 1 method has the best total RNA recovery of any of the five methods.

sis. For all applications involving enzymatic reactions, the RNA from the Example 1 method was further purified using a sodium acetate/ethanol precipitation step. Specifically, RNA samples isolated using either the Example 1 method or the TRIzol® Max™ RNA isolation procedures were compared in an RT-PCR experiment to amplify the *E. coli* lpp mRNA. As shown in FIG. 3, the Example 1 method RNA gave results that were comparable to those obtained with the TRIzol® Max™ isolated RNA and reflected the relative abundances shown in Table 2. In addition, RNA isolated from the Example 1 method was used in determining the 5' and 3' ends of the pheU and pheV tRNA transcripts by initially ligating the 5' and 3' ends of the transcripts. The RNA isolated from the Example 1 method has also been used successfully in various primer extension experiments.

The RT-PCR was performed using the following method. SK4390 (rph-1 ΔrppH) was grown with shaking at 37° C. in Luria broth supplemented with thymine (50 µg/mL) and kanamycin (25 µg/mL) until 20 Klett units above background (No. 42 green filter). The culture was then shifted to 44° C. for two hours. The culture was maintained at 80 Kletts units above background by making periodic dilutions with pre-warmed Luria broth. RNA was extracted using the Example 1 method described above or with the TRIzol® Max™ method. Both RNA samples were subjected to sodium acetate/ethanol precipitation, DNA removal with the DNA-free kit™ (Ambion) and a final sodium acetate/ethanol precipitation. RNA was quantified using a NanoDrop™ (Thermo Scientific; Waltham, Mass.). Five hundred ng of each RNA sample were run on 1% Agarose-Tris-acetate-EDTA gel and visualized with ethidium bromide for quality and quantity verification. Five µg of each RNA sample was reverse transcribed using a lpp gene-specific primer (Lpp538: CAGGTACTATTACT-TGGGGTAT) (SEQ ID NO: 1) using Superscript® III reverse transcriptase (Invitrogen). The cDNAs were amplified using two gene-specific primers (Lpp538 and LppPCR1: GCTA-CATGGAGATTAACT) (SEQ ID NO:2) in a GoTaq® Green Master Mix (Promega; Fitchburg, Wis.). The PCT products were run on a 2% agarose-Tris-acetate-EDTA gel and visu-

TABLE 3

|  | Catrimide/ LiCl | TRIzol® Max™ Bacteria | RNeasy® Protect Bacteria | RiboPure™ Bacteria | Example 1 |
| --- | --- | --- | --- | --- | --- |
| Approx. cost/sample (U.S. dollars) | 0.20 | 4.20 | 8.10 | 7.14 | 0.03 |
| Approx. yield from $10^8$ *E. coli* cells (µg) | 35 | 27 | 35 | 15 | 60 |
| Approx. duration of isolation (min) | 60 | 60 | 40 | 40 | 15 |
| RNA size range for efficient isolation (nt) | 76-5700 | 76-3000 | 200-3000 | 300->5700 | 76->5700 |

Cost data are based on the list price of chemicals or extraction kits. The approximate yield is the average yield of RNA isolated in this study based on $10^8$ cells. All of these methods have the ability to handle more than $10^8$ cells. For example, the RiboPure Bacteria kit recommends using $10^9$ cells. The approximate duration of RNA isolation is based on the time required for each individual step using a small number of samples. The RNA size range data is based on the sizes of specific RNAs detected by Northern analysis (FIG. 2).

Using the Example 1 Method for Primer Extension and RT-PCR Experiments

The isolated RNA from the Example 1 method was further tested for its functionality in commonly applied techniques such as RT-PCT, RNA ligation, and primer extension analyalized with ethidium bromide. For additional confirmation that the lpp cDNA had been amplified, Southern blot analysis was performed by transferring the PCT products to a Nytran® SuPerCharge membrane using a Turboblotter™ (Schleicher and Schuell Bioscience, Inc.; Keene, N.H.). The membrane was probed with $^{32}$P-5'-end-labeled lpp specific oligonucleotide (LPP562A: CGCTTGCGTTCACGTCG) (SEQ ID NO:3) and scanned with a Phosphorimager Storm™ 840 (GE Healthcare; Waukesha, Wis.).

Example 2

The methods can be used to isolate high-quality RNA from cells derived from higher eukaryotes such as human tissue samples. The cultured cells are pelleted and suspended in an appropriate volume of RNA extraction solution, whereas tissue samples are directly suspended in RNA extraction solution, and homogenized by vortexing with zirconium beads within the extraction solution. The extraction solution consists of 50% formamide by volume, 1% β-mercaptoethanol by volume, 1% SDS by weight/volume, and 18 mM EDTA. The samples are then heated at 95° C. for 5 minutes, and subsequently centrifuged at 16,000×g for 5 minutes at room temperature. The RNA in the supernatant is then precipitated using sodium acetate/ethanol, and suspended in RNase-free water. Alternatively, the RNA containing supernatant is further purified by column chromatography, and suspended in RNase-free water.

The methods and kits of the appended claims are not limited in scope by the specific methods and kits described herein, which are intended as illustrations of a few aspects of the claims and any methods and kits that are functionally equivalent are within the scope of this disclosure. Various modifications of the methods and kits in addition to those shown and described herein are intended to fall within the scope of the appended claims. Further, while only certain representative methods and kits, and aspects of these methods and kits are specifically described, other methods and kits and combinations of various features of the methods and kits are intended to fall within the scope of the appended claims, even if not specifically recited. Thus, a combination of steps, elements, components, or constituents may be explicitly mentioned herein; however, all other combinations of steps, elements, components, and constituents are included, even though not explicitly stated.

What is claimed is:

1. A method for isolating cellular ribonucleic acid (RNA), comprising:
   (a) suspending cells in an extraction solution comprising formamide in an amount of at least 40% by volume of the extraction solution;
   (b) incubating the cells and formamide mixture of step (a); and
   (c) pelleting cell debris, DNA, and protein to form an RNA-containing supernatant.

2. The method of claim 1, further comprising adding zirconium beads prior to incubating the mixture.

3. The method of claim 1, further comprising pelleting the cells prior to suspending the cells in the extraction solution.

4. The method of claim 1, wherein the extraction solution further comprises a reducing agent, an anionic detergent, a chelating agent, or a mixture thereof.

5. The method of claim 4, wherein the reducing agent comprises β-mercaptoethanol or dithiothreitol.

6. The method of claim 5, wherein the β-mercaptoethanol is present in the extraction solution in an amount of less than 5% by volume of the extraction solution.

7. The method of claim 5, wherein the β-mercaptoethanol is present in the extraction solution in an amount of less than 2% by volume of the extraction solution.

8. The method of claim 5, wherein the dithiothreitol is present in the extraction solution at a concentration of from 50 μM to 1 M.

9. The method of claim 4, wherein the anionic detergent comprises sodium dodecyl sulfate.

SEQUENCE LISTING

<160> NUMBER OF SEQ ID NOS: 3

<210> SEQ ID NO 1
<211> LENGTH: 22
<212> TYPE: DNA
<213> ORGANISM: Artificial Sequence
<220> FEATURE:
<223> OTHER INFORMATION: Synthetic Construct

<400> SEQUENCE: 1
caggtactat tacttggggt at                                              22

<210> SEQ ID NO 2
<211> LENGTH: 18
<212> TYPE: DNA
<213> ORGANISM: Artificial Sequence
<220> FEATURE:
<223> OTHER INFORMATION: Synthetic Construct

<400> SEQUENCE: 2
gctacatgga gattaact                                                   18

<210> SEQ ID NO 3
<211> LENGTH: 17
<212> TYPE: DNA
<213> ORGANISM: Artificial Sequence
<220> FEATURE:
<223> OTHER INFORMATION: Synthetic Construct

<400> SEQUENCE: 3
cgcttgcgtt cacgtcg                                                    17

10. The method of claim 4, wherein the anionic detergent is present in the extraction solution in an amount of less than 5% by weight/volume of the extraction solution.

11. The method of claim 4, wherein the anionic detergent is present in the extraction solution in an amount of less than 0.05% by weight/volume of the extraction solution.

12. The method of claim 4, wherein the chelating agent comprises EDTA.

13. The method of claim 4, wherein the chelating agent is present in the extraction solution at a concentration of from 0.5 mM to 50 mM.

14. The method of claim 4, wherein the chelating agent is present in the extraction solution at a concentration of 18 mM.

15. The method of claim 1, wherein the extraction solution is substantially free from quaternary amine surfactants.

16. The method of claim 1, wherein the incubating step is performed at a temperature of from 10° C. to 140° C.

17. The method of claim 1, wherein the incubating step is performed at a temperature of 95° C.

* * * * *